United States Patent
Matsumura et al.

(10) Patent No.: US 11,530,286 B2
(45) Date of Patent: *Dec. 20, 2022

(54) SULFOBETAINE-BASED PROTEIN AGGREGATION INHIBITOR FOR USE IN PREVENTING AGGREGATION OF A PROTEIN

(71) Applicants: OSAKA ORGANIC CHEMICAL INDUSTRY LTD., Osaka (JP); JAPAN ADVANCED INSTITUTE OF SCIENCE AND TECHNOLOGY, Nomi (JP)

(72) Inventors: Kazuaki Matsumura, Nomi (JP); Rajan Robin, Nomi (JP); Yoko Taniyama, Hakusan (JP); Yoshiyuki Saruwatari, Osaka (JP)

(73) Assignees: OSAKA ORGANIC CHEMICAL INDUSTRY LTD., Osaka (JP); JAPAN ADVANCED INSTITUTE OF SCIENCE AND TECHNOLOGY, Nomi (JP)

( * ) Notice: Subject to any disclaimer, the term of this patent is extended or adjusted under 35 U.S.C. 154(b) by 904 days.

This patent is subject to a terminal disclaimer.

(21) Appl. No.: 16/305,576

(22) PCT Filed: May 30, 2017

(86) PCT No.: PCT/JP2017/020075
§ 371 (c)(1),
(2) Date: Nov. 29, 2018

(87) PCT Pub. No.: WO2017/209121
PCT Pub. Date: Dec. 7, 2017

(65) Prior Publication Data
US 2020/0332044 A1    Oct. 22, 2020

(30) Foreign Application Priority Data

May 31, 2016  (JP) ............................ JP2016-108846

(51) Int. Cl.
*C08F 291/14*    (2006.01)
*C12N 9/36*    (2006.01)
*C12N 9/96*    (2006.01)

(52) U.S. Cl.
CPC .......... *C08F 291/14* (2013.01); *C12N 9/2462* (2013.01); *C12N 9/96* (2013.01); *C12Y 302/01017* (2013.01); *C08F 2810/20* (2013.01)

(58) Field of Classification Search
None
See application file for complete search history.

(56) References Cited

U.S. PATENT DOCUMENTS 10,995,160 B2 *   5/2021   Matsumura ........... C08F 120/60
2018/0118859 A1   5/2018   Matsumura et al.
2019/0161563 A1   5/2019   Matsumura et al.

FOREIGN PATENT DOCUMENTS

JP    2006-343201 A       12/2006
WO    WO 2016/181975 A1   11/2016

OTHER PUBLICATIONS

Ivanov et al. Colloids and Surfaces A: Physicochem. Eng. Aspects 282-283 (2006) 129-133 (Year: 2006).*
Atanasov et al., "Double Hydrophilic Block Zwitterionic Copolymer as an Acid Phosphatase Folding Helper," *Godishnik na Sofiiskiya Universitet "Sv. Kliment Okhridski," Khimicheski Fakultet*, 98-99: 327-335 (2006).
Durand-Gasselin et al., "Colloidal stability of zwitterionic polymer-grafted gold nanoparticles in water," *J. Colloid Interface Sci.*, 434: 188-194 (2014).
Ivanov et al., "Chaperone-Like Effect of Polyzwitterions on the Interaction of C1q with IgG," *Zeitschrift für Naturforschung C.*, 64(1-2): 149-154 (2009).
Ning et al., "Characteristics of zwitterionic sulfobetaine acrylamide polymer and the hydrogels prepared by free-radical polymerization and effects of physical and chemical crosslinks on the UCST," *Reactive & Functional Polymers*, 73(7): 969-978 (2013).
Rajan et al., "A zwitterionic polymer as a novel inhibitor of protein aggregation," *J. Mater. Chem. B*, 3: 5683-5689 (2015).
Rajan et al., "Inhibition of protein aggregation by zwitterionic polymer-based core-shell nanogels," *Sci. Rep.*, 7: 45777 (Apr. 4, 2017).
Yoshioika et al., "Thermostatic Characteristic of Betaine Polymers and Gels," *SCEJ 7th Autumn Meeting (Okayama, 2005)*, Abstract A319 (Mar. 18, 2006).
Japanese Patent Office, International Search Report in International Patent Application No. PCT/JP2017/020075 (dated Aug. 29, 2017).
U.S. Appl. No. 16/313,405, filed Dec. 26, 2018.
Japanese Patent Office, International Search Report in International Patent Application No. PCT/JP2017/023879 (dated Sep. 26, 2017).

* cited by examiner

*Primary Examiner* — Christian L Fronda
(74) *Attorney, Agent, or Firm* — Leydig, Voit & Mayer, Ltd.

(57) ABSTRACT

The present invention provides a protein aggregation inhibitor for use in preventing aggregation of a protein, containing a crosslinked polymer obtained by polymerizing polymerizable polymer components containing a sulfobetaine polymer obtained by polymerizing monomer components containing a sulfobetaine monomer, the sulfobetaine monomer, and a crosslinkable monomer.

6 Claims, No Drawings

SULFOBETAINE-BASED PROTEIN AGGREGATION INHIBITOR FOR USE IN PREVENTING AGGREGATION OF A PROTEIN

CROSS-REFERENCE TO RELATED APPLICATIONS

This patent application is the U.S. national phase of International Patent Application No. PCT/JP2017/020075, filed May 30, 2017, which claims the benefit of Japanese Patent Application No. 2016-108846, filed on May 31, 2016, which are incorporated by reference in their entireties herein.

TECHNICAL FIELD

The present invention relates to a protein aggregation inhibitor. The protein aggregation inhibitor of the present invention maintains lysozyme activity and prevents aggregation of protein. Thus, use thereof for various applications where inhibition of protein aggregation is desired such as preservative for enzyme, antibody drug, in vivo amyloid aggregation inhibitor and the like is expected.

BACKGROUND ART

As a protein aggregation inhibitor capable of preventing aggregation of protein under acidic conditions, a protein aggregation inhibitor containing at least one kind of non-ionic surfactant selected from the group consisting of polyoxyethylene distyrenated phenyl ether, polyoxyethylene myristyl ether and polyoxyethylene(10) octylphenyl ether has been proposed (e.g., patent document 1).

Since the aforementioned protein aggregation inhibitor can inhibit, to some extent, aggregation of protein under acidic conditions since it uses a surfactant.

In recent years, however, the development of a protein aggregation inhibitor superior in the protein aggregation inhibitory effect even without using a surfactant has been desired.

DOCUMENT LIST

[Patent Document]
patent document 1: JP-A-2006-343201

SUMMARY OF THE INVENTION

Problems to be Solved by the Invention

The present invention has been made in view of the aforementioned prior art, and the problem thereof is provision of a protein aggregation inhibitor that maintains lysozyme activity and is superior in a protein aggregation inhibitory effect even without using a surfactant.

Means of Solving the Problems

The present invention relates to the following.
[1] A protein aggregation inhibitor for use in preventing aggregation of a protein, the inhibitor comprising a crosslinked polymer obtained by polymerizing polymerizable polymer components comprising
  a sulfobetaine polymer obtained by polymerizing monomer components comprising a sulfobetaine monomer, the aforementioned sulfobetaine monomer, and
  a crosslinkable monomer.

[2] The protein aggregation inhibitor of the aforementioned [1], wherein the monomer components further comprise a thiocarbonylthio group-containing compound having at least one carboxyl group.
[3] The protein aggregation inhibitor of the aforementioned [2], wherein the thiocarbonylthio group-containing compound having at least one carboxyl group has the formula (II):

$$R^5-S-C(=S)-S-R^6 \quad (II)$$

wherein $R^5$ is an alkyl group optionally having a carboxyl group, and $R^6$ is a carboxyl group-containing alkyl group optionally having a cyano group.
[4] The protein aggregation inhibitor of the aforementioned [2], wherein the thiocarbonylthio group-containing compound having at least one carboxyl group is at least one selected from the group consisting of 2-(dodecylthiocarbonothioylthio)-2-methylpropionic acid, 4-[(2-carboxyethylsulfanylthiocarbonyl)sulfanyl]-4-cyanopentanoic acid, 2-{[(2-carboxyethyl)sulfanylthiocarbonyl]sulfanyl}propanoic acid, 4-cyano-4-[(dodecylsulfanylthiocarbonyl)sulfanyl]pentanoic acid, 2-[(dodecylsulfanylthiocarbonyl)sulfanyl]propanoic acid, and methyl-4-cyano-4-[(dodecylsulfanylthiocarbonyl)sulfanyl]pentanoic acid.
[5] The protein aggregation inhibitor of the aforementioned [2], wherein the thiocarbonylthio group-containing compound having at least one carboxyl group is 2-(dodecylthiocarbonothioylthio)-2-methylpropionic acid.
[6] The protein aggregation inhibitor of any one of the aforementioned [2] to [5], wherein an amount of the thiocarbonylthio group-containing compound having at least one carboxyl group is 0.003 to 0.5 mol per 1 mol of the sulfobetaine monomer in the monomer components.
[7] The protein aggregation inhibitor of any one of the aforementioned [2] to [5], wherein an amount of the thiocarbonylthio group-containing compound having at least one carboxyl group is 0.01 to 0.5 mol per 1 mol of the sulfobetaine monomer in the monomer components.
[8] The protein aggregation inhibitor of any one of the aforementioned [2] to [5], wherein an amount of the thiocarbonylthio group-containing compound having at least one carboxyl group is 0.03 to 0.3 mol per 1 mol of the sulfobetaine monomer in the monomer components.
[9] The protein aggregation inhibitor of any one of the aforementioned [1] to [8], wherein the sulfobetaine monomer is represented by the formula (I):

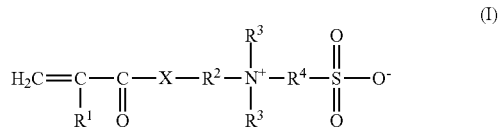

wherein $R^1$ is a hydrogen atom or a methyl group, $R^2$ is an alkylene group having 1-4 carbon atoms, $R^3$ is an alkyl group having 1-4 carbon atoms, $R^4$ is an alkylene group having 1-4 carbon atoms, and X is an —NH— group or an —O— group.
[10] The protein aggregation inhibitor of the aforementioned [9], wherein $R^1$ is a hydrogen atom.
[11] The protein aggregation inhibitor of the aforementioned [9] or [10], wherein $R^2$ is a —(CH$_2$)— group, a —(CH$_2$)$_2$— group or a —(CH$_2$)$_3$— group.
[12] The protein aggregation inhibitor of the aforementioned [9] or [10], wherein $R^2$ is a —(CH$_2$)$_3$— group.

[13] The protein aggregation inhibitor of any one of the aforementioned [9] to [12], wherein $R^3$ is a methyl group, an ethyl group or a propyl group.
[14] The protein aggregation inhibitor of any one of the aforementioned [9] to [12], wherein $R^3$ is a methyl group or an ethyl group.
[15] The protein aggregation inhibitor of any one of the aforementioned [9] to [12], wherein $R^3$ is a methyl group.
[16] The protein aggregation inhibitor of any one of the aforementioned [9] to [15], wherein $R^4$ is a —$(CH_2)$— group, a —$(CH_2)_2$— group or a —$(CH_2)_3$— group.
[17] The protein aggregation inhibitor of any one of the aforementioned [9] to [15], wherein $R^4$ is a —$(CH_2)_3$— group.
[18] The protein aggregation inhibitor of any one of the aforementioned [9] to [17], wherein X is an —NH— group.
[19] The protein aggregation inhibitor of any one of the aforementioned [1] to [18], wherein the sulfobetaine polymer has a number average molecular weight of 3,000 to 100,000.
[20] The protein aggregation inhibitor of any one of the aforementioned [1] to [18], wherein the sulfobetaine polymer has a number average molecular weight of 5,000 to 50,000.
[21] The protein aggregation inhibitor of any one of the aforementioned [1] to [20], wherein an amount of the sulfobetaine polymer is 5 to 30 parts by mass per 100 parts by mass of the sulfobetaine monomer in the polymerizable polymer components.
[22] The protein aggregation inhibitor of any one of the aforementioned [1] to [20], wherein an amount of the sulfobetaine polymer is 10 to 25 parts by mass per 100 parts by mass of the sulfobetaine monomer in the polymerizable polymer components.
[23] The protein aggregation inhibitor of any one of the aforementioned [1] to [22], wherein the crosslinkable monomer is at least one selected from the group consisting of a (meth)acrylamide compound having two or more (meth)acryloyl groups, a (meth)acrylate compound having two or more (meth)acryloyl groups, an amine compound having two or more carbon-carbon double bonds and an aromatic compound having two or more carbon-carbon double bonds.
[24] The protein aggregation inhibitor of any one of the aforementioned [1] to [22], wherein the crosslinkable monomer is at least one selected from the group consisting of a (meth)acrylamide compound having two or more (meth)acryloyl groups, a (meth)acrylate compound having two or more (meth)acryloyl groups and an amine compound having two or more carbon-carbon double bonds.
[25] The protein aggregation inhibitor of any one of the aforementioned [1] to [22], wherein the crosslinkable monomer is at least one selected from the group consisting of a (meth)acrylamide compound having two or more (meth)acryloyl groups and a (meth)acrylate compound having two or more (meth)acryloyl groups.
[26] The protein aggregation inhibitor of any one of the aforementioned [1] to [22], wherein the crosslinkable monomer is at least one selected from the group consisting of ethylene diacrylate, ethylene dimethacrylate, ethylene glycol diacrylate, ethylene glycol dimethacrylate, propylene glycol diacrylate, propylene glycol dimethacrylate, diethylene glycol diacrylate, diethylene glycol dimethacrylate, dipropylene glycol diacrylate, dipropylene glycol dimethacrylate, triethylene glycol diacrylate, triethylene glycol dimethacrylate, tripropylene glycol diacrylate, tripropylene glycol dimethacrylate, tetraethylene glycol diacrylate, tetraethylene glycol dimethacrylate, tetrapropylene glycol diacrylate, tetrapropylene glycol dimethacrylate, 1,4-butanediol diacrylate and 1,4-butanediol dimethacrylate.
[27] The protein aggregation inhibitor of any one of the aforementioned [1] to [22], wherein the crosslinkable monomer is at least one selected from the group consisting of ethylene glycol diacrylate and ethylene glycol dimethacrylate.
[28] The protein aggregation inhibitor of any one of the aforementioned [1] to [27], wherein an amount of the crosslinkable monomer is 0.5 to 10 parts by mass per 100 parts by mass of the sulfobetaine monomer in the polymerizable polymer components.
[29] The protein aggregation inhibitor of any one of the aforementioned [1] to [27], wherein an amount of the crosslinkable monomer is 1 to 5 parts by mass per 100 parts by mass of the sulfobetaine monomer in the polymerizable polymer components.
[30] The protein aggregation inhibitor of any one of the aforementioned [1] to [29], wherein the polymerizable polymer components further comprise a hydrophobic monomer.
[31] The protein aggregation inhibitor of the aforementioned [30], wherein the hydrophobic monomer is at least one selected from the group consisting of an alkyl (meth)acrylate having an alkyl group having 1 to 18 carbon atoms, a cycloalkyl (meth)acrylate having a cycloalkyl group having 6 to 12 carbon atoms and an aryl (meth)acrylate having an aryl group having 6 to 12 carbon atoms.
[32] The protein aggregation inhibitor of the aforementioned [30], wherein the hydrophobic monomer is an alkyl (meth)acrylate having an alkyl group having 1 to 18 carbon atoms.
[33] The protein aggregation inhibitor of the aforementioned [30], wherein the hydrophobic monomer is an alkyl (meth)acrylate having an alkyl group having 1 to 6 carbon atoms.
[34] The protein aggregation inhibitor of any one of the aforementioned [30] to [33], wherein an amount of the hydrophobic monomer is 0.5 to 10 parts by mass per 100 parts by mass of the sulfobetaine monomer in the polymerizable polymer components.
[35] The protein aggregation inhibitor of any one of the aforementioned [30] to [33], wherein an amount of the hydrophobic monomer is 1 to 5 parts by mass per 100 parts by mass of the sulfobetaine monomer in the polymerizable polymer components.
[36] A method of preventing aggregation of a protein, comprising mixing the protein, a solvent or dispersion medium, and the protein aggregation inhibitor of any one of the aforementioned [1] to [35].
[37] The method of the aforementioned [36], wherein the protein aggregation inhibitor is used such that an amount of the crosslinked polymer contained in the protein aggregation inhibitor is 10 to 200 parts by mass per 1 part by mass of the protein.
[38] The method of the aforementioned [36], wherein the protein aggregation inhibitor is used such that an amount of the crosslinked polymer contained in the protein aggregation inhibitor is 50 to 100 parts by mass per 1 part by mass of the protein.
[39] The method of any one of the aforementioned [36] to [38], wherein the protein, the solvent or dispersion medium, and the protein aggregation inhibitor are mixed such that a content of the protein in the mixture comprising the protein, the solvent or dispersion medium, and the protein aggregation inhibitor is 0.001 to 20 mass %.
[40] The method of any one of the aforementioned [36] to [38], wherein the protein, the solvent or dispersion medium, and the protein aggregation inhibitor are mixed such that a content of the protein in the mixture comprising the protein, the solvent or dispersion medium, and the protein aggregation inhibitor is 0.01 to 10 mass %.

[41] A method of producing a protein aggregation inhibitor for use in preventing aggregation of a protein and comprising a crosslinked polymer, the method comprising
  polymerizing monomer components comprising a sulfobetaine monomer, and
  polymerizing polymerizable polymer components comprising the resulting sulfobetaine polymer, the aforementioned sulfobetaine monomer, and a crosslinkable monomer.

[42] The method of the aforementioned [41], wherein the monomer components are polymerized in the presence of a thiocarbonylthio group-containing compound having at least one carboxyl group.

[43] The method of the aforementioned [42], wherein the thiocarbonylthio group-containing compound having at least one carboxyl group has the formula (II):

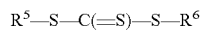 (II)

wherein $R^5$ is an alkyl group optionally having a carboxyl group, and $R^6$ is a carboxyl group-containing alkyl group optionally having a cyano group.

[44] The method of the aforementioned [42], wherein the thiocarbonylthio group-containing compound having at least one carboxyl group is at least one selected from the group consisting of 2-(dodecylthiocarbonothioylthio)-2-methylpropionic acid, 4-[(2-carboxyethylsulfanylthiocarbonyl)sulfanyl]-4-cyanopentanoic acid, 2-{[(2-carboxyethyl)sulfanylthiocarbonyl]sulfanyl}propanoic acid, 4-cyano-4-[(dodecylsulfanylthiocarbonyl)sulfanyl]pentanoic acid, 2-[(dodecylsulfanylthiocarbonyl)sulfanyl]propanoic acid, and methyl-4-cyano-4-[(dodecylsulfanylthiocarbonyl)sulfanyl]pentanoic acid.

[45] The method of the aforementioned [42], wherein the thiocarbonylthio group-containing compound having at least one carboxyl group is 2-(dodecylthiocarbonothioylthio)-2-methylpropionic acid.

[46] The method of any one of the aforementioned [42] to [45], wherein an amount of the thiocarbonylthio group-containing compound having at least one carboxyl group is 0.003 to 0.5 mol per 1 mol of the sulfobetaine monomer in the monomer components.

[47] The method of any one of the aforementioned [42] to [45], wherein an amount of the thiocarbonylthio group-containing compound having at least one carboxyl group is 0.01 to 0.5 mol per 1 mol of the sulfobetaine monomer in the monomer components.

[48] The method of any one of the aforementioned [42] to [45], wherein an amount of the thiocarbonylthio group-containing compound having at least one carboxyl group is 0.03 to 0.3 mol per 1 mol of the sulfobetaine monomer in the monomer components.

[49] The method of any one of the aforementioned [41] to [48], wherein the sulfobetaine monomer is represented by the formula (I):

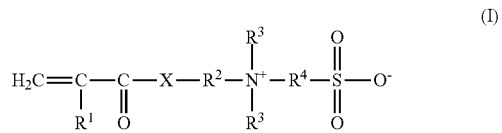 (I)

wherein $R^1$ is a hydrogen atom or a methyl group, $R^2$ is an alkylene group having 1-4 carbon atoms, $R^3$ is an alkyl group having 1-4 carbon atoms, $R^4$ is an alkylene group having 1-4 carbon atoms, and X is an —NH— group or an —O— group.

[50] The method of the aforementioned [49], wherein $R^1$ is a hydrogen atom.

[51] The method of the aforementioned [49] or [50], wherein $R^2$ is a —$(CH_2)$— group, a —$(CH_2)_2$— group or a —$(CH_2)_3$— group.

[52] The method of the aforementioned [49] or [50], wherein $R^2$ is a —$(CH_2)_3$— group.

[53] The method of any one of the aforementioned [49] to [52], wherein $R^3$ is a methyl group, an ethyl group or a propyl group.

[54] The method of any one of the aforementioned [49] to [52], wherein $R^3$ is a methyl group or an ethyl group.

[55] The method of any one of the aforementioned [49] to [52], wherein $R^3$ is a methyl group.

[56] The method of any one of the aforementioned [49] to [55], wherein $R^4$ is a —$(CH_2)$— group, a —$(CH_2)_2$— group or a —$(CH_2)_3$— group.

[57] The method of any one of the aforementioned [49] to [55], wherein $R^4$ is a —$(CH_2)_3$— group.

[58] The method of any one of the aforementioned [49] to [57], wherein X is an —NH— group.

[59] The method of any one of the aforementioned [41] to [58], wherein the sulfobetaine polymer has a number average molecular weight of 3,000 to 100,000.

[60] The method of any one of the aforementioned [41] to [58], wherein the sulfobetaine polymer has a number average molecular weight of 5,000 to 50,000.

[61] The method of any one of the aforementioned [41] to [60], wherein an amount of the sulfobetaine polymer is 5 to 30 parts by mass per 100 parts by mass of the sulfobetaine monomer in the polymerizable polymer components.

[62] The method of any one of the aforementioned [41] to [60], wherein an amount of the sulfobetaine polymer is 10 to 25 parts by mass per 100 parts by mass of the sulfobetaine monomer in the polymerizable polymer components.

[63] The method of any one of the aforementioned [41] to [62], wherein the crosslinkable monomer is at least one selected from the group consisting of a (meth)acrylamide compound having two or more (meth)acryloyl groups, a (meth)acrylate compound having two or more (meth)acryloyl groups, an amine compound having two or more carbon-carbon double bonds and an aromatic compound having two or more carbon-carbon double bonds.

[64] The method of any one of the aforementioned [41] to [62], wherein the crosslinkable monomer is at least one selected from the group consisting of a (meth)acrylamide compound having two or more (meth)acryloyl groups, a (meth)acrylate compound having two or more (meth)acryloyl groups and an amine compound having two or more carbon-carbon double bonds.

[65] The method of any one of the aforementioned [41] to [62], wherein the crosslinkable monomer is at least one selected from the group consisting of a (meth)acrylamide compound having two or more (meth)acryloyl groups and a (meth)acrylate compound having two or more (meth)acryloyl groups.

[66] The method of any one of the aforementioned [41] to [62], wherein the crosslinkable monomer is at least one selected from the group consisting of ethylene diacrylate, ethylene dimethacrylate, ethylene glycol diacrylate, ethylene glycol dimethacrylate, propylene glycol diacrylate, propylene glycol dimethacrylate, diethylene glycol diacrylate, diethylene glycol dimethacrylate, dipropylene glycol diacrylate, dipropylene glycol dimethacrylate, triethylene glycol diacrylate, triethylene glycol dimethacrylate, tripropylene glycol diacrylate, tripropylene glycol dimethacrylate, tetraethylene glycol diacrylate, tetraethylene glycol dimethacrylate, tetrapropylene glycol diacrylate, tetrapropylene glycol dimethacrylate, 1,4-butanediol diacrylate and 1,4-butanediol dimethacrylate.

[67] The method of any one of the aforementioned [41] to [62], wherein the crosslinkable monomer is at least one selected from the group consisting of ethylene glycol diacrylate and ethylene glycol dimethacrylate.

[68] The method of any one of the aforementioned [41] to [67], wherein an amount of the crosslinkable monomer is 0.5 to 10 parts by mass per 100 parts by mass of the sulfobetaine monomer in the polymerizable polymer components.

[69] The method of any one of the aforementioned [41] to [67], wherein an amount of the crosslinkable monomer is 1 to 5 parts by mass per 100 parts by mass of the sulfobetaine monomer in the polymerizable polymer components.

[70] The method of any one of the aforementioned [41] to [69], wherein the polymerizable polymer components further comprise a hydrophobic monomer.

[71] The method of the aforementioned [70], wherein the hydrophobic monomer is at least one selected from the group consisting of an alkyl (meth)acrylate having an alkyl group having 1 to 18 carbon atoms, a cycloalkyl (meth)acrylate having a cycloalkyl group having 6 to 12 carbon atoms and an aryl (meth)acrylate having an aryl group having 6 to 12 carbon atoms.

[72] The method of the aforementioned [70], wherein the hydrophobic monomer is an alkyl (meth)acrylate having an alkyl group having 1 to 18 carbon atoms.

[73] The method of the aforementioned [70], wherein the hydrophobic monomer is an alkyl (meth)acrylate having an alkyl group having 1 to 6 carbon atoms.

[74] The method of any one of the aforementioned [70] to [73], wherein an amount of the hydrophobic monomer is 0.5 to 10 parts by mass per 100 parts by mass of the sulfobetaine monomer in the polymerizable polymer components.

[75] The method of any one of the aforementioned [70] to [73], wherein an amount of the hydrophobic monomer is 1 to 5 parts by mass per 100 parts by mass of the sulfobetaine monomer in the polymerizable polymer components.

Effect of the Invention

According to the present invention, a protein aggregation inhibitor that maintains lysozyme activity and is superior in a protein aggregation inhibitory effect is provided.

DESCRIPTION OF EMBODIMENTS

The protein aggregation inhibitor of the present invention is a protein aggregation inhibitor used to prevent aggregation of a protein, as mentioned above, and characteristically contains a crosslinked polymer obtained by polymerizing polymerizable polymer components containing a sulfobetaine polymer obtained by polymerizing monomer components containing a sulfobetaine monomer, the aforementioned sulfobetaine monomer, and a crosslinkable monomer.

A crosslinked polymer can be prepared, for example, by polymerizing polymerizable polymer components containing a sulfobetaine polymer produced by polymerizing monomer components containing a sulfobetaine monomer, the aforementioned sulfobetaine monomer, and a crosslinkable monomer.

In the present invention, the sulfobetaine monomer contained in the monomer components used for producing the sulfobetaine polymer, and the sulfobetaine monomer contained in the polymerizable polymer components used for producing the crosslinked polymer may be the same or different. It is preferable that these sulfobetaine monomers are the same.

Examples of the sulfobetaine monomer include a sulfobetaine monomer represented by the formula (I):

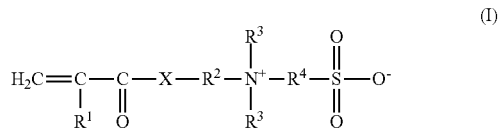

and the like. However, the present invention is not limited to such example alone. The sulfobetaine monomer represented by the formula (I) may be used alone, or two or more kinds thereof may be used in combination.

In the formula (I), $R^1$ is a hydrogen atom or a methyl group, preferably a hydrogen atom.

$R^2$ is an alkylene group having 1-4 carbon atoms. Examples of the alkylene group having 1-4 carbon atoms include a methylene group (—$CH_2$—), an ethylene group (—$(CH_2)_2$—), a propylene group (e.g., —$(CH_2)_3$—) and a butylene group (e.g., —$(CH_2)_4$). Among these groups, a methylene group, an ethylene group and a propylene group are preferable, a —$(CH_2)$— group, a —$(CH_2)_2$— group and a —$(CH_2)_3$— group are more preferable, and a —$(CH_2)_3$— group is more preferable for obtaining a protein aggregation inhibitor that maintains lysozyme activity and is superior in a protein aggregation inhibitory effect.

$R^3$ is an alkyl group having 1-4 carbon atoms. Examples of the alkyl group having 1-4 carbon atoms include a methyl group, an ethyl group, a propyl group and a butyl group. Among these groups, a methyl group, an ethyl group and a propyl group are preferable, a methyl group and an ethyl group are more preferable, and a methyl group is further preferable for obtaining a protein aggregation inhibitor that maintains lysozyme activity and is superior in a protein aggregation inhibitory effect.

$R^4$ is an alkylene group having 1-4 carbon atoms. Examples of the alkylene group having 1-4 carbon atoms include a methylene group (—$CH_2$—), an ethylene group (—$(CH_2)_2$—), a propylene group (e.g., —$(CH_2)_3$—) and a butylene group (e.g., —$(CH_2)_4$—). Among these groups, a methylene group, an ethylene group and a propylene group are preferable, a —$(CH_2)$— group, a —$(CH_2)_2$— group and a —$(CH_2)_3$— group are more preferable, and a —$(CH_2)_3$— group is further preferable for obtaining a protein aggregation inhibitor that maintains lysozyme activity and is superior in a protein aggregation inhibitory effect.

X is an —NH— group or an —O— group. Of these groups, an —NH— group is preferable for obtaining a protein aggregation inhibitor that maintains lysozyme activity and is superior in a protein aggregation inhibitory effect.

Examples of the sulfobetaine monomer represented by the formula (I) include 3-[(3-(meth)acrylamidoalkyl)dialkylammonio]alkane-1-sulfonates such as 3-[(3-acrylamidomethyl)dimethylammonio]ethane-1-sulfonate, 3-[(3-methacrylamidomethyl)dimethylammonio]ethane-1-sulfonate, 3-[(3-acrylamidomethyl)diethylammonio]ethane-1-sulfonate, 3-[(3-methacrylamidomethyl)diethylammonio]ethane-1-sulfonate, 3-[(3-acrylamidomethyl)dipropylammonio]ethane-1-sulfonate, 3-[(3-methacrylamidomethyl)dipropylammonio]ethane-1-sulfonate, 3-[(3-acrylamidomethyl)

dibutylammonio]ethane-1-sulfonate, 3-[(3-methacrylamidomethyl)dibutylammonio]ethane-1-sulfonate, 3-[(3-acrylamidoethyl)dimethylammonio]ethane-1-sulfonate, 3-[(3-methacrylamidoethyl)dimethylammonio]ethane-1-sulfonate, 3-[(3-acrylamidoethyl)diethylammonio]ethane-1-sulfonate, 3-[(3-methacrylamidoethyl)diethylammonio]ethane-1-sulfonate, 3-[(3-acrylamidoethyl)dipropylammonio]ethane-1-sulfonate, 3-[(3-methacrylamidoethyl)dipropylammonio]ethane-1-sulfonate, 3-[(3-acrylamidoethyl)dibutylammonio]ethane-1-sulfonate, 3-[(3-methacrylamidoethyl)dibutylammonio]ethane-1-sulfonate, 3-[(3-acrylamidopropyl)dimethylammonio]ethane-1-sulfonate, 3-[(3-methacrylamidopropyl)dimethylammonio]ethane-1-sulfonate, 3-[(3-acrylamidopropyl)diethylammonio]ethane-1-sulfonate, 3-[(3-methacrylamidopropyl)diethylammonio]ethane-1-sulfonate, 3-[(3-acrylamidopropyl)dipropylammonio]ethane-1-sulfonate, 3-[(3-methacrylamidopropyl)dipropylammonio]ethane-1-sulfonate, 3-[(3-acrylamidopropyl)dibutylammonio]ethane-1-sulfonate, 3-[(3-methacrylamidopropyl)dibutylammonio]ethane-1-sulfonate, 3-[(3-acrylamidobutyl)dimethylammonio]ethane-1-sulfonate, 3-[(3-methacrylamidobutyl)dimethylammonio]ethane-1-sulfonate, 3-[(3-acrylamidobutyl)diethylammonio]ethane-1-sulfonate, 3-[(3-methacrylamidobutyl)diethylammonio]ethane-1-sulfonate, 3-[(3-acrylamidobutyl)dipropylammonio]ethane-1-sulfonate, 3-[(3-methacrylamidobutyl)dipropylammonio]ethane-1-sulfonate, 3-[(3-acrylamidobutyl)dibutylammonio]ethane-1-sulfonate, 3-[(3-methacrylamidobutyl)dibutylammonio]ethane-1-sulfonate, 3-[(3-acrylamidomethyl)dimethylammonio]propane-1-sulfonate, 3-[(3-methacrylamidomethyl)dimethylammonio]propane-1-sulfonate, 3-[(3-acrylamidomethyl)diethylammonio]propane-1-sulfonate, 3-[(3-methacrylamidomethyl)diethylammonio]propane-1-sulfonate, 3-[(3-acrylamidomethyl)dipropylammonio]propane-1-sulfonate, 3-[(3-methacrylamidomethyl)dipropylammonio]propane-1-sulfonate, 3-[(3-acrylamidomethyl)dibutylammonio]propane-1-sulfonate, 3-[(3-methacrylamidomethyl)dibutylammonio]propane-1-sulfonate, 3-[(3-acrylamidoethyl)dimethylammonio]propane-1-sulfonate, 3-[(3-methacrylamidoethyl)dimethylammonio]propane-1-sulfonate, 3-[(3-acrylamidoethyl)diethylammonio]propane-1-sulfonate, 3-[(3-methacrylamidoethyl)diethylammonio]propane-1-sulfonate, 3-[(3-acrylamidoethyl)dipropylammonio]propane-1-sulfonate, 3-[(3-methacrylamidoethyl)dipropylammonio]propane-1-sulfonate, 3-[(3-acrylamidoethyl)dibutylammonio]propane-1-sulfonate, 3-[(3-methacrylamidoethyl)dibutylammonio]propane-1-sulfonate, 3-[(3-acrylamidopropyl)dimethylammonio]propane-1-sulfonate, 3-[(3-methacrylamidopropyl)dimethylammonio]propane-1-sulfonate, 3-[(3-acrylamidopropyl)diethylammonio]propane-1-sulfonate, 3-[(3-methacrylamidopropyl)diethylammonio]propane-1-sulfonate, 3-[(3-acrylamidopropyl)dipropylammonio]propane-1-sulfonate, 3-[(3-methacrylamidopropyl)dipropylammonio]propane-1-sulfonate, 3-[(3-acrylamidopropyl)dibutylammonio]propane-1-sulfonate, 3-[(3-methacrylamidopropyl)dibutylammonio]propane-1-sulfonate, 3-[(3-acrylamidobutyl)dimethylammonio]propane-1-sulfonate, 3-[(3-methacrylamidobutyl)dimethylammonio]propane-1-sulfonate, 3-[(3-acrylamidobutyl)diethylammonio]propane-1-sulfonate, 3-[(3-methacrylamidobutyl)diethylammonio]propane-1-sulfonate, 3-[(3-acrylamidobutyl)dipropylammonio]propane-1-sulfonate, 3-[(3-methacrylamidobutyl)dipropylammonio]propane-1-sulfonate, 3-[(3-acrylamidobutyl)dibutylammonio]propane-1-sulfonate, 3-[(3-methacrylamidobutyl)dibutylammonio]propane-1-sulfonate, 3-[(3-acrylamidomethyl)dimethylammonio]butane-1-sulfonate, 3-[(3-methacrylamidomethyl)dimethylammonio]butane-1-sulfonate, 3-[(3-acrylamidomethyl)diethylammonio]butane-1-sulfonate, 3-[(3-methacrylamidomethyl)diethylammonio]butane-1-sulfonate, 3-[(3-acrylamidomethyl)dipropylammonio]butane-1-sulfonate, 3-[(3-methacrylamidomethyl)dipropylammonio]butane-1-sulfonate, 3-[(3-acrylamidomethyl)dibutylammonio]butane-1-sulfonate, 3-[(3-methacrylamidomethyl)dibutylammonio]butane-1-sulfonate, 3-[(3-acrylamidoethyl)dimethylammonio]butane-1-sulfonate, 3-[(3-methacrylamidoethyl)dimethylammonio]butane-1-sulfonate, 3-[(3-acrylamidoethyl)diethylammonio]butane-1-sulfonate, 3-[(3-methacrylamidoethyl)diethylammonio]butane-1-sulfonate, 3-[(3-acrylamidoethyl)dipropylammonio]butane-1-sulfonate, 3-[(3-methacrylamidoethyl)dipropylammonio]butane-1-sulfonate, 3-[(3-acrylamidoethyl)dibutylammonio]butane-1-sulfonate, 3-[(3-methacrylamidoethyl)dibutylammonio]butane-1-sulfonate, 3-[(3-acrylamidopropyl)dimethylammonio]butane-1-sulfonate, 3-[(3-methacrylamidopropyl)dimethylammonio]butane-1-sulfonate, 3-[(3-acrylamidopropyl)diethylammonio]butane-1-sulfonate, 3-[(3-3-[(3-acrylamidopropyl)dipropylammonio]butane-1-sulfonate, 3-[(3-methacrylamidopropyl)dipropylammonio]butane-1-sulfonate, 3-[(3-acrylamidopropyl)dibutylammonio]butane-1-sulfonate, 3-[(3-methacrylamidopropyl)dibutylammonio]butane-1-sulfonate, 3-[(3-acrylamidobutyl)dimethylammonio]butane-1-sulfonate, 3-[(3-methacrylamidobutyl)dimethylammonio]butane-1-sulfonate, 3-[(3-acrylamidobutyl)diethylammonio]butane-1-sulfonate, 3-[(3-methacrylamidobutyl)diethylammonio]butane-1-sulfonate, 3-[(3-acrylamidobutyl)dipropylammonio]butane-1-sulfonate, 3-[(3-methacrylamidobutyl)dipropylammonio]butane-1-sulfonate, 3-[(3-acrylamidobutyl)dibutylammonio]butane-1-sulfonate, 3-[(3-methacrylamidobutyl)dibutylammonio]butane-1-sulfonate and the like;

3-[(3-(meth)acryloyloxyalkyl)dialkylammonio]alkane-1-sulfonates such as 3-[(3-acryloyloxymethyl)dimethylammonio]ethane-1-sulfonate, 3-[(3-methacryloyloxymethyl)dimethylammonio]ethane-1-sulfonate, 3-[(3-acryloyloxymethyl)diethylammonio]ethane-1-sulfonate, 3-[(3-methacryloyloxymethyl)diethylammonio]ethane-1-sulfonate, 3-[(3-acryloyloxymethyl)dipropylammonio]ethane-1-sulfonate, 3-[(3-methacryloyloxymethyl)dipropylammonio]ethane-1-sulfonate, 3-[(3-acryloyloxymethyl)dibutylammonio]ethane-1-sulfonate, 3-[(3-methacryloyloxymethyl)dibutylammonio]ethane-1-sulfonate, 3-[(3-acryloyloxyethyl)dimethylammonio]ethane-1-sulfonate, 3-[(3-methacryloyloxyethyl)dimethylammonio]ethane-1-sulfonate, 3-[(3-acryloyloxyethyl)diethylammonio]ethane-1-sulfonate, 3-[(3-methacryloyloxyethyl)diethylammonio]ethane-1-sulfonate, 3-[(3-acryloyloxyethyl)dipropylammonio]ethane-1-sulfonate, 3-[(3-methacryloyloxyethyl)dipropylammonio]ethane-1-sulfonate, 3-[(3-acryloyloxyethyl)dibutylammonio]ethane-1-sulfonate, 3-[(3-methacryloyloxyethyl)dibutylammonio]ethane-1-sulfonate, 3-[(3-acryloyloxypropyl)dimethylammonio]ethane-1-sulfonate, 3-[(3-methacryloyloxypropyl)dimethylammonio]ethane-1-sulfonate, 3-[(3-acryloyloxypropyl)diethylammonio]ethane-1-sulfonate, 3-[(3-methacryloyloxypropyl)diethylammonio]ethane-1-sulfonate, 3-[(3-acryloyloxypropyl)dipropylammonio]ethane-1-sulfonate, 3-[(3-methacryloyloxypropyl)dipropylammonio]ethane-1-sulfonate, 3-[(3-acryloyloxypropyl)dibutylammonio]ethane-1-sulfonate, 3-[(3-methacryloyloxypropyl)dibutylammonio]ethane-1-sulfonate, 3-[(3-acryloyloxybutyl)dimethylammonio]ethane-1-sulfonate, 3-[(3-methacryloyloxybutyl)dimethylammonio]ethane-1-sulfonate, 3-[(3-acryloyloxybutyl)diethylammonio]ethane-1-sulfonate, 3-[(3-methacryloyloxybutyl)diethylammonio]ethane-1-sulfonate, 3-[(3-acryloyloxybutyl)dipropylammonio]ethane-1-sulfonate, 3-[(3-methacryloyloxybutyl)dipropylammonio]ethane-1-sulfonate, 3-[(3-acryloyloxybutyl)dibutylammonio]ethane-1-sulfonate, 3-[(3-methacryloyloxybutyl)dibutylammonio]ethane-1-sulfonate, 3-[(3-acryloyloxymethyl)dimethylammonio]propane-1-sulfonate, 3-[(3-methacryloyloxymethyl)dimethylammonio]propane-1-sulfonate, 3-[(3-acryloyloxymethyl)diethylammonio]propane-1-sulfonate, 3-[(3-methacryloyloxymethyl)diethylammonio]propane-1-sulfonate, 3-[(3-acryloyloxymethyl)dipropylammonio]propane-1-sulfonate, 3-[(3-methacryloyloxymethyl)dipropylamrnonio]propane-1-sulfonate, 3-[(3-acryloyloxymethyl)dibutylammonio]propane-1-sulfonate, 3-[(3-methacryloyloxymethyl)dibutylammonio]propane-1-sulfonate, 3-[(3-acryloyloxyethyl)dimethylammonio]propane-1-sulfonate, 3-[(3-methacryloyloxyethyl)dimethylammonio]propane-1-sulfonate, 3-[(3-acryloyloxyethyl)diethylammonio]propane-1-sulfonate, 3-[(3-methacryloyloxyethyl)diethylammonio]propane-1-sulfonate, 3-[(3-acryloyloxyethyl)dipropylammonio]propane-1-sulfonate, 3-[(3-methacryloyloxyethyl)dipropylammonio]propane-1-sulfonate, 3-[(3-acryloyloxyethyl)dibutylammonio]propane-1-sulfonate, 3-[(3-methacryloyloxyethyl)dibutylammonio]propane-1-sulfonate, 3-[(3-acryloyloxypropyl)dimethylammonio]propane-1-sulfonate, 3-[(3-methacryloyloxypropyl)dimethylammonio]propane-1-sulfonate, 3-[(3-acryloyloxypropyl)diethylammonio]propane-1-sulfonate, 3-[(3-methacryloyloxypropyl)diethylammonio]propane-1-sulfonate, 3-[(3-acryloyloxypropyl)dipropylammonio]propane-1-sulfonate, 3-[(3-methacryloyloxypropyl)dipropylammonio]propane-1-sulfonate, 3-[(3-acryloyloxypropyl)dibutylammonio]propane-1-sulfonate, 3-[(3-methacryloyloxypropyl)dibutylammonio]propane-1-sulfonate, 3-[(3-acryloyloxybutyl)dimethylammonio]propane-1-sulfonate, 3-[(3-methacryloyloxybutyl)dimethylammonio]propane-1-sulfonate, 3-[(3-acryloyloxybutyl)diethylammonio]propane-1-sulfonate, 3-[(3-methacryloyloxybutyl)diethylammonio]propane-1-sulfonate, 3-[(3-acryloyloxybutyl)dipropylammonio]propane-1-sulfonate, 3-[(3-methacryloyloxybutyl)dipropylammonio]propane-1-sulfonate, 3-[(3-acryloyloxybutyl)dibutylammonio]propane-1-sulfonate, 3-[(3-methacryloyloxybutyl)dibutylammonio]propane-1-sulfonate, 3-[(3-acryloyloxymethyl)dimethylammonio]butane-1-sulfonate, 3-[(3-methacryloyloxymethyl)dimethylammonio]butane-1-sulfonate, 3-[(3-acryloyloxymethyl)diethylammonio]butane-1-sulfonate, 3-[(3-methacryloyloxymethyl)diethylammonio]butane-1-sulfonate, 3-[(3-acryloyloxymethyl)dipropylammonio]butane-1-sulfonate, 3-[(3-methacryloyloxymethyl)dipropylammonio]butane-1-sulfonate, 3-[(3-acryloyloxymethyl)dibutylammonio]butane-1-sulfonate, 3-[(3-methacryloyloxymethyl)dibutylammonio]butane-1-sulfonate, 3-[(3-acryloyloxyethyl)dimethylammonio]butane-1-sulfonate, 3-[(3-methacryloyloxyethyl)dimethylammonio]butane-1-sulfonate, 3-[(3-acryloyloxyethyl)diethylammonio]butane-1-sulfonate, 3-[(3-methacryloyloxyethyl)diethylammonio]butane-1-sulfonate, 3-[(3-acryloyloxyethyl)dipropylammonio]butane-1-sulfonate, 3-[(3-methacryloyloxyethyl)dipropylammonio]butane-1-sulfonate, 3-[(3-acryloyloxyethyl)dibutylammonio]butane-1-sulfonate, 3-[(3-methacryloyloxyethyl)dibutylammonio]butane-1-sulfonate, 3-[(3-acryloyloxypropyl)dimethylammonio]butane-1-sulfonate, 3-[(3-methacryloyloxypropyl)dimethylammonio]butane-1-sulfonate, 3-[(3-acryloyloxypropyl)diethylammonio]butane-1-sulfonate, 3-[(3-methacryloyloxypropyl)diethylammonio]butane-1-sulfonate, 3-[(3-acryloyloxypropyl)dipropylammonio]butane-1-sulfonate, 3-[(3-methacryloyloxypropyl)dipropylammonio]butane-1-sulfonate, 3-[(3-acryloyloxypropyl)dibutylammonio]butane-1-sulfonate, 3-[(3-methacryloyloxypropyl)dibutylammonio]butane-1-sulfonate, 3-[(3-acryloyloxybutyl)dimethylammonio]butane-1-sulfonate, 3-[(3-methacryloyloxybutyl)dimethylammonio]butane-1-sulfonate, 3-[(3-acryloyloxybutyl)diethylammonio]butane-1-sulfonate, 3-[(3-methacryloyloxybutyl)diethylammonio]butane-1-sulfonate, 3-[(3-acryloyloxybutyl)dipropylammonio]butane-1-sulfonate, 3-[(3-methacryloyloxybutyl)dipropylammonio]butane-1-sulfonate, 3-[(3-acryloyloxybutyl)dibutylammonio]butane-1-sulfonate, 3-[(3-methacryloyloxybutyl)dibutylammonio]butane-1-sulfonate and the like; and the like. However, the present invention is not limited to these examples alone. These sulfobetaine monomers may each be used alone, or two or more kinds thereof may be used in combination.

In the present invention, "(meth)acrylamide" means acrylamide or methacrylamide, acrylamide and methacrylamide may each be used alone, or may be used in combination.

The "(meth)acryloyloxy" means acryloyloxy or methacryloyloxy, and acryloyloxy and methacryloyloxy may each be used alone, or may be used in combination.

The "(meth)acrylate" means acrylate or methacrylate, and acrylate and methacrylate may each be used alone, or may be used in combination.

The "(meth)acrylic acid" means acrylic acid or methacrylic acid, and acrylic acid and methacrylic acid may each be used alone, or may be used in combination.

In the present invention, a water-soluble monomer can be used as the monomer components besides a sulfobetaine monomer, as long as the object of the present invention is not inhibited.

The water-soluble monomer means a monomer showing dissolution property of not less than 50 g in 100 g of water at 25° C. Examples of the water-soluble monomer include (meth)acrylamide, N-vinylpyrrolidone, (meth)acrylonitrile, 2-hydroxyethyl (meth)acrylate, 2-hydroxypropyl (meth)acrylate, 4-hydroxybutyl (meth)acrylate, polyethylene glycol (meth)acrylate, methoxypolyethylene glycol (meth)acrylate, ethoxypolyethylene glycol (meth)acrylate, polyethylene glycol di(meth)acrylate, N-(meth)acrylmorpholide, N-methoxymethyl(meth)acrylamide, N-hydroxymethyl(meth)acrylamide, N-hydroxyethyl(meth)acrylamide, 2-hydroxyethyl vinyl ether, N,N-dimethyl(meth)acrylamide, N,N-diethyl(meth)acrylamide, N-monomethyl(meth)acrylamide, N-monoethyl(meth)acrylamide and the like. However, the present invention is not limited to these examples alone. These water-soluble monomers may each be used alone, or two or more kinds thereof may be used in combination. Among these water-soluble monomers, (meth)acrylamide, N-vinylpyrrolidone and (meth)acrylonitrile are preferable, and (meth)acrylamide and N-vinylpyrrolidone are more preferable for obtaining a protein aggregation inhibitor that maintains lysozyme activity and is superior in a protein aggregation inhibitory effect.

The monomer components may contain a water-insoluble monomer as long as the object of the present invention is not inhibited. The water-insoluble monomer means a monomer showing dissolution property of less than 50 g in 100 g of water at 25° C.

Examples of the water-insoluble monomer include alkyl (meth)acrylate, alkoxy group-containing (meth)acrylate, alicyclic group-containing (meth)acrylate, aryl group-containing (meth)acrylate, aromatic monomer other than aryl group-containing (meth)acrylate and the like. However, the present invention is not limited to these examples alone.

These water-insoluble monomers may each be used alone, or two or more kinds thereof may be used in combination.

Examples of the alkyl (meth)acrylate include methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, sec-butyl (meth)acrylate, n-pentyl (meth)acrylate, n-hexyl (meth)acrylate, n-octyl (meth)acrylate, isooctyl (meth)acrylate, n-nonyl (meth)acrylate, isononyl (meth)acrylate, 2-ethylhexyl (meth)acrylate, decyl (meth)acrylate, dodecyl (meth)acrylate, tridecyl (meth)acrylate, tetradecyl (meth)acrylate, hexadecyl (meth)acrylate, octadecyl (meth)acrylate, isostearyl (meth)acrylate, eicosyl (meth)acrylate, behenyl (meth)acrylate, tetrahydrofurfuryl (meth)acrylate and the like. However, the present invention is not limited to these examples alone. These alkyl (meth)acrylates may each be used alone, or two or more kinds thereof may be used in combination.

Examples of the alkoxy group-containing (meth)acrylate include 2-methoxyethyl (meth)acrylate, 2-ethoxyethyl (meth)acrylate, methoxyethylene glycol (meth)acrylate, ethylcarbitol (meth)acrylate and the like. However, the present invention is not limited to these examples alone. These alkoxy group-containing (meth)acrylates may each be used alone, or two or more kinds thereof may be used in combination.

Examples of the alicyclic group-containing (meth)acrylate include cyclohexyl (meth)acrylate, tert-butylcyclohexyl (meth)acrylate, isobornyl (meth)acrylate, dicyclopentanyl (meth)acrylate, dicyclopentenyl (meth)acrylate, adamantyl (meth)acrylate, dicyclopentenyl (meth)acrylate, and the like. However, the present invention is not limited to these examples alone. These alicyclic group-containing (meth)acrylates may each be used alone, or two or more kinds thereof may be used in combination.

Examples of the aryl group-containing (meth)acrylate include (meth)acrylates having an aryl group having 6-15 carbon atoms, such as benzyl (meth)acrylate, phenoxyethyl (meth)acrylate and the like, and the like. However, the present invention is not limited to these examples alone. These aryl group-containing (meth)acrylates may each be used alone, or two or more kinds thereof may be used in combination.

Examples of the aromatic monomer other than aryl group-containing (meth)acrylate include styrene, α-methylstyrene and the like. However, the present invention is not limited to these examples alone. These aromatic monomers may each be used alone, or two or more kinds thereof may be used in combination.

The total amount of the water-soluble monomer and the water-insoluble monomer other than the sulfobetaine monomer is preferably less than 50 mol %, more preferably less than 30 mol %, further preferably less than 10 mol %, relative to the total monomer components. It is particularly preferable that the monomer components do not contain the water-soluble monomer and the water-insoluble monomer other than the sulfobetaine monomer.

When monomer components are polymerized, it is preferable to use a chain transfer agent to prepare the molecular weight of the obtained sulfobetaine polymer. Examples of the preferable chain transfer agent include a thiocarbonylthio group-containing compound having at least one carboxyl group and the like.

In the present invention, monomer components can be polymerized in the presence of a thiocarbonylthio group-containing compound having at least one carboxyl group. More specifically, for example, a thiocarbonylthio group-containing compound having at least one carboxyl group is contained in monomer components, and the monomer components containing the thiocarbonylthio group-containing compound having at least one carboxyl group can be polymerized.

Examples of the thiocarbonylthio group-containing compound having at least one carboxyl group include a thiocarbonylthio group-containing compound represented by the formula (II):

$$R^5\text{—}S\text{—}C(=S)\text{—}S\text{—}R^6 \qquad (II)$$

wherein $R^5$ is an alkyl group optionally having a carboxyl group, and $R^6$ is a carboxyl group-containing alkyl group optionally having a cyano group, and the like. The thiocarbonylthio group-containing compound represented by the formula (II) may be used alone, or two or more kinds thereof may be used in combination.

In the formula (II), $R^5$ is an alkyl group optionally having a carboxyl group. It is preferably an alkyl group having 1-18 carbon atoms or an alkyl group having 1-4 carbon atoms and optionally having a carboxyl group, more preferably an alkyl group having 1-12 carbon atoms or an alkyl group having 1-4 carbon atoms and optionally having a carboxyl group, for, obtaining a protein aggregation inhibitor that maintains lysozyme activity and is superior in a protein aggregation inhibitory effect.

$R^6$ is a carboxyl group-containing alkyl group optionally having a cyano group. It is preferably a carboxyl group-containing alkyl group having 1-4 carbon atoms and optionally having a cyano group, more preferably a group optionally having a straight chain or a branched chain, and represented by the formula: —$R^7$—COOH wherein $R^7$ is an alkylene group having 1-4 carbon atoms, for obtaining a protein aggregation inhibitor that maintains lysozyme activity and is superior in a protein aggregation inhibitory effect.

Examples of the thiocarbonylthio group-containing compound having at least one carboxyl group include 2-(dodecylthiocarbonothioylthio)-2-methylpropionic acid, 4-[(2-carboxyethylsulfanylthiocarbonyl)sulfanyl]-4-cyanopentanoic acid, 2-{[(2-carboxyethyl)sulfanylthiocarbonyl]sulfanyl}propanoic acid, 4-cyano-4-[(dodecylsulfanylthiocarbonyl)sulfanyl]pentanoic acid, 2-[(dodecylsulfanylthiocarbonyl)sulfanyl]propanoic acid, methyl-4-cyano-4-[(dodecylsulfanylthiocarbonyl)sulfanyl]pentanoic acid and the like. However, the present invention is not limited to these examples alone. These thiocarbonylthio group-containing compounds having at least one carboxyl group may each be used alone, or two or more kinds thereof may be used in combination. As the thiocarbonylthio group-containing compound having at least one carboxyl group, 2-(dodecylthiocarbonothioylthio)-2-methylpropionic acid is preferable.

The amount of the thiocarbonylthio group-containing compound having at least one carboxyl group per 1 mol of the sulfobetaine monomer in the monomer components is preferably 0.003-0.5 mol, preferably 0.01-0.5 mol, more preferably 0.03-0.3 mol, for obtaining a protein aggregation inhibitor that maintains lysozyme activity and is superior in a protein aggregation inhibitory effect.

Examples of a method of polymerizing monomer components include bulk polymerization method, solution polymerization method, emulsion polymerization method, suspension polymerization method and the like. However, the present invention is not limited to these examples alone. Of these polymerization methods, the solution polymerization method is preferable.

When monomer components are polymerized by the solution polymerization method, for example, the monomer components can be polymerized by dissolving the monomer components and, where necessary, a chain transfer agent such as the thiocarbonylthio group-containing compound having at least one carboxyl group or the like in solvent, and adding a polymerization initiator to the obtained solution while stirring the solution. Alternatively, the monomer components can be polymerized by dissolving a polymerization initiator in solvent, and adding monomer components to the obtained solution while stirring the solution.

Examples of the solvent include water, a hydrophilic organic solvent, a mixed solvent of water and a hydrophilic organic solvent and the like. The present invention is not limited by the kind of the solvent.

Examples of the hydrophilic organic solvent include monovalent aliphatic alcohols having 1-4 carbon atoms such as methanol, ethanol, propanol and the like; ketones such as acetone, methyl ethyl ketone and the like; ethers such as tetrahydrofuran, dioxane, diglyme and the like; amides such as N,N-dimethylformamide, N,N-dimethylacetamide, N-methyl-2-pyrrolidone, 1,3-dimethyl-2-imidazolidinone and the like; sulfur-containing organic solvents such as dimethyl sulfoxide, sulfolane and the like, and the like. However, the present invention is not limited to these examples alone. These hydrophilic organic solvents may each be used alone, or two or more kinds thereof may be used in combination. Among these hydrophilic organic solvents, the monovalent aliphatic alcohols having 1-4 carbon atoms are preferable, methanol, ethanol and propanol are more preferable, methanol and ethanol are further preferable, for obtaining a protein aggregation inhibitor that maintains lysozyme activity and is superior in a protein aggregation inhibitory effect.

While the amount of the solvent is not particularly limited, it is generally preferably 50-400 parts by mass, more preferably 100-350 parts by mass, per 100 parts by mass of the monomer components.

When the monomer components are polymerized, a polymerization initiator is preferably used. Examples of the polymerization initiator include azobisisobutyronitrile, azoisobutyronitrile, azo methyl isobutyrate, azobisdimethylvaleronitrile, benzoyl peroxide, potassium persulfate, ammonium persulfate, benzophenone derivative, phosphineoxide derivative, benzoketone derivative, phenyl thioether derivative, azide derivative, diazo derivative, disulfide derivative and the like. However, the present invention is not limited to these examples alone. These polymerization initiators may each be used alone, or two or more kinds thereof may be used in combination. While the amount of the polymerization initiator is not particularly limited, it is generally preferably about 0.05-20 parts by mass per 100 parts by mass of the monomer components.

The polymerization reaction temperature and atmosphere when the monomer components are polymerized are not particularly limited. Generally, the polymerization reaction temperature is about 50-120° C. The atmosphere at the time of polymerization reaction is preferably inert gas atmosphere such as nitrogen gas and the like. While the polymerization reaction time of the monomer components cannot be decided unconditionally since it varies depending on the temperature of polymerization reaction and the like, it is generally about 3-20 hr.

A sulfobetaine polymer can be obtained by polymerizing monomer components as mentioned above.

The number average molecular weight of the sulfobetaine polymer is preferably 3,000-100,000, more preferably 5,000-50,000, for obtaining a protein aggregation inhibitor that maintains lysozyme activity and is superior in a protein aggregation inhibitory effect. The number average molecular weight of the sulfobetaine polymer is a value measured based on the method described in the section of the following Example (Preparation Example 1).

When a sulfobetaine polymer is prepared by solution polymerization in the presence of an aqueous solvent, the reaction solution containing the sulfobetaine polymer can be used as it is as a protein aggregation inhibitor. Where necessary, a solvent such as water, a water-soluble alcohol such as methanol, ethanol or the like, a mixed solvent thereof, or the like may be used to wash the sulfobetaine polymer.

Then, polymerizable polymer components containing the sulfobetaine polymer obtained above, the aforementioned sulfobetaine monomer and a crosslinkable monomer are polymerized to give a crosslinked polymer.

Examples of the sulfobetaine monomer used for polymerizable polymer components include those similar to the sulfobetaine monomer used for monomer components.

The amount of the sulfobetaine polymer is preferably 5-30 parts by mass, more preferably 10-25 parts by mass, per 100 parts by mass of the sulfobetaine monomer in the polymerizable polymer components, for obtaining a protein aggregation inhibitor that maintains lysozyme activity and is superior in a protein aggregation inhibitory effect.

Examples of the crosslinkable monomer include a (meth)acrylamide compound having two or more (meth)acryloyl groups, a (meth)acrylate compound having two or more (meth)acryloyl groups, an amine compound having two or more carbon-carbon double bonds, an aromatic compound having two or more carbon-carbon double bonds and the like. The present invention is not limited to these examples alone. The crosslinkable monomer may be used alone, or two or more kinds thereof may be used in combination.

Specific examples of the crosslinkable monomer include multifunctional monomers such as (meth)acrylamide compounds having two or more (preferably two) (meth)acryloyl groups such as alkylenebis(meth)acrylamides having an alkylene group having 1 to 4 carbon atoms, such as methylenebisacrylamide, methylenebismethacrylamide and the like; (meth)acrylate compounds having two or more (preferably two or three) (meth)acryloyl groups such as ethylene diacrylate, ethylene dimethacrylate, ethylene glycol diacrylate, ethylene glycol dimethacrylate, propylene glycol diacrylate, propylene glycol dimethacrylate, diethylene glycol diacrylate, diethylene glycol dimethacrylate, dipropylene glycol diacrylate, dipropylene glycol dimethacrylate, triethylene glycol diacrylate, triethylene glycol dimethacrylate, tripropylene glycol diacrylate, tripropylene glycol dimethacrylate, tetraethylene glycol diacrylate, tetraethylene glycol dimethacrylate, tetrapropylene glycol diacrylate, tetrapropylene glycol dimethacrylate, 1,4-butanediol diacrylate, 1,4-butanediol dimethacrylate, 1,6-hexanediol diacrylate, 1,6-hexanediol dimethacrylate, 1,9-nonanediol diacrylate, 1,9-nonanediol dimethacrylate, 2-n-butyl-2-ethyl-1,3-propanediol diacrylate, 2-n-butyl-2-ethyl-1,3-propanediol dimethacrylate, trimethylolpropane triacrylate, trimethylolpropane trimethacrylate, pentaerythritol triacrylate, pentaerythritol trimethacrylate and the like; amine compounds having two or more (preferably two or three) carbon-carbon double bonds such as diallylamine, triallylamine and the like; aromatic compounds having two or more (preferably two or three) carbon-carbon double bonds such as divinylbenzene, diallylbenzene and the like, and the like. The present invention is not limited to these examples alone.

These crosslinkable monomers may each be used alone, or two or more kinds thereof may be used in combination.

Among the crosslinkable monomers, a (meth)acrylamide compound having two or more (meth)acryloyl groups, a (meth)acrylate compound having two or more (meth)acryloyl groups, an amine compound having two or more carbon-carbon double bonds and an aromatic compound having two or more carbon-carbon double bonds is preferable, a (meth)acrylamide compound having two or more (meth)acryloyl groups, a (meth)acrylate compound having two or more (meth)acryloyl groups and an amine compound having two or more carbon-carbon double bonds are more preferable, a (meth)acrylamide compound having two or more (meth)acryloyl groups and a (meth)acrylate compound having two or more (meth)acryloyl groups are further preferable, ethylene diacrylate, ethylene dimethacrylate, ethylene glycol diacrylate, ethylene glycol dimethacrylate, propylene glycol diacrylate, propylene glycol dimethacrylate, diethylene glycol diacrylate, diethylene glycol dimethacrylate, dipropylene glycol diacrylate, dipropylene glycol dimethacrylate, triethylene glycol diacrylate, triethylene glycol dimethacrylate, tripropylene glycol diacrylate, tripropylene glycol dimethacrylate, tetraethylene glycol diacrylate, tetraethylene glycol dimethacrylate, tetrapropylene glycol diacrylate, tetrapropylene glycol dimethacrylate, 1,4-butanediol diacrylate and 1,4-butanediol dimethacrylate are particularly preferable, and ethylene glycol diacrylate and ethylene glycol dimethacrylate are most preferable, for obtaining a protein aggregation inhibitor that maintains lysozyme activity and is superior in a protein aggregation inhibitory effect. These crosslinkable monomers may each be used alone, or two or more kinds thereof may be used in combination.

The amount of the crosslinkable monomer is preferably 0.5-10 parts by mass, more preferably 1-5 parts by mass, per 100 parts by mass of the sulfobetaine monomer in the polymerizable polymer components, for obtaining a protein aggregation inhibitor that maintains lysozyme activity and is superior in a protein aggregation inhibitory effect.

It is preferable that a hydrophobic monomer is contained in the polymerizable polymer components for obtaining a protein aggregation inhibitor that maintains lysozyme activity and is superior in a protein aggregation inhibitory effect. The hydrophobic monomer may be used alone, or two or more kinds thereof may be used in combination.

Examples of the hydrophobic monomer include monofunctional monomers such as alkyl (meth)acrylates having an alkyl group having 1 to 18 carbon atoms such as methyl acrylate, methyl methacrylate, ethyl acrylate, ethyl methacrylate, butyl acrylate, butyl methacrylate, isobutyl acrylate, isobutyl methacrylate, tert-butyl acrylate, tert-butyl methacrylate, neopentyl acrylate, neopentyl methacrylate, octyl acrylate, octyl methacrylate, lauryl acrylate, lauryl methacrylate, lauryl acrylate, lauryl methacrylate, stearyl acrylate, stearyl methacrylate, cetyl acrylate, cetyl methacrylate and the like; cycloalkyl (meth)acrylates having a cycloalkyl group having 6 to 12 carbon atoms such as cyclohexyl acrylate, cyclohexyl methacrylate and the like; aryl (meth)acrylates having an aryl group having 6 to 12 carbon atoms such as benzyl acrylate, benzyl methacrylate and the like; alkoxyalkyl (meth)acrylates having an alkoxyalkyl group having 2 to 8 carbon atoms such as methoxyethyl acrylate, methoxyethyl methacrylate, methoxybutyl acrylate, methoxybutyl methacrylate and the like; alkyl (meth)acrylamides having an alkyl group having 1 to 12 carbon atoms such as N-methylacrylamide, N-methylmethacrylamide, N-ethylacrylamide, N-ethylmethacrylamide, N-propylacrylamide, N-propylmethacrylamide, N-isopropylacrylamide, N-isopropylmethacrylamide, N-tert-butylacrylamide, N-tert-butylmethacrylamide, N-octylacrylamide, N-octylmethacrylamide, N,N-dimethylacrylamide, N,N-dimethylmethacrylamide, N,N-diethylacrylamide, N,N-diethylmethacrylamide and the like: alkoxy(meth)acrylamides having an alkoxy group having 1 to 6 carbon atoms such as N-butoxymethylacrylamide, N-butoxy methylmethacrylamide and the like; (meth)acryloylmorpholines such as acryloylmorpholine, methacryloylmorpholine and the like; diacetone (meth)acrylamides such as diacetone acrylamide, diacetone methacrylamide and the like; styrene monomers such as styrene, methylstyrene and the like; fatty acid alkyls having an alkyl group having 1 to 4 carbon atoms other than alkyl (meth)acrylates such as methyl itaconate, ethyl itaconate and the like; nitrogen atom-containing monomers such as N-vinylpyrrolidone, N-vinylcaprolactam and the like, and the like. The present invention is not limited to these examples alone. These hydrophobic monomers may each be used alone, or two or more kinds thereof may be used in combination.

Among the hydrophobic monomers, alkyl (meth)acrylates having an alkyl group having 1 to 18 carbon atoms, cycloalkyl (meth)acrylates having a cycloalkyl group having 6 to 12 carbon atoms and aryl (meth)acrylates having an aryl group having 6 to 12 carbon atoms are preferable, alkyl (meth)acrylates having an alkyl group having 1 to 18 carbon atoms are more preferable, and alkyl (meth)acrylates having an alkyl group having 1 to 6 carbon atoms are further preferable, for obtaining a protein aggregation inhibitor that maintains lysozyme activity and is superior in a protein aggregation inhibitory effect.

The amount of the hydrophobic monomer is preferably 0.5-10 parts by mass, more preferably 1-5 parts by mass, per 100 parts by mass of the sulfobetaine monomer in the polymerizable polymer components, for obtaining a protein aggregation inhibitor that maintains lysozyme activity and is superior in a protein aggregation inhibitory effect.

Examples of a method of polymerizing polymerizable polymer components include bulk polymerization method, solution polymerization method, emulsion polymerization method, suspension polymerization method and the like. However, the present invention is not limited to these examples alone. Of these polymerization methods, the solution polymerization method is preferable.

When polymerizable polymer components are polymerized by the solution polymerization method, for example, the polymerizable polymer components can be polymerized by dissolving the polymerizable polymer components in an aqueous solvent, and adding a polymerization initiator to the obtained solution while stirring the solution. Alternatively, the polymerizable polymer components can be polymerized by dissolving a polymerization initiator in an aqueous solvent, and adding polymerizable polymer components to the obtained solution while stirring the solution.

The aqueous solvent is water or a mixed solvent of water and a hydrophilic organic solvent other than water. The content of water in the aqueous solvent is generally not less than 50 mass % and not more than 100 mass %.

Examples of the hydrophilic organic solvent include monovalent aliphatic alcohols having 1-4 carbon atoms such as methanol, ethanol, propanol and the like; ketones such as acetone, methyl ethyl ketone and the like; ethers such as tetrahydrofuran, dioxane, diglyme and the like; amides such as N,N-dimethylformamide, N,N-dimethylacetamide, N-methyl-2-pyrrolidone, 1,3-dimethyl-2-imidazolidinone and the like; sulfur-containing organic solvents such as dimethyl sulfoxide, sulfolane and the like, and the like. However, the present invention is not limited to these examples alone. These hydrophilic organic solvents may each be used alone, or two or more kinds thereof may be used in combination. Among these hydrophilic organic solvents, monovalent aliphatic alcohols having 1 to 4 carbon atoms are preferable, methanol, ethanol and propanol are more preferable, and methanol and ethanol are further preferable, for obtaining a protein aggregation inhibitor that maintains lysozyme activity and is superior in a protein aggregation inhibitory effect.

While the amount of the aqueous solvent is not particularly limited, it is generally preferably 100-3000 parts by mass, more preferably 1000-25000 parts by mass, per 100 parts by mass of the polymerizable polymer components.

When the polymerizable polymer components are polymerized, a polymerization initiator is preferably used. Examples of the polymerization initiator include azo initiator, peroxide initiator and the like. The present invention is not limited to these examples alone.

Examples of the azo initiator include 2,2'-azobisisobutyronitrile, 2,2'-azobis-methylbutyronitrile, 2,2'-azobis-2,4-dimethylvaleronitrile, 1,1'-azobis-cyclohexanecarbonitrile, dimethyl-2,2'-azobisisobutyrate, 4,4'-azobis-(4-cyanovaleric acid), 2,2'-azobis-(2-amidinopropene) dihydrochloride, 2-tert-butylazo-2-cyanopropane, 2,2'-azobis-(2-methyl-propionamide) dihydrate, 2,2'-azobis[2-(2-imidazolin-2-yl)propene], 2,2'-azobis(2,2,4-trimethylpentane) and the like. The present invention is not limited to these examples alone.

Examples of the peroxide initiator include ketone peroxides such as benzoyl peroxide, methyl ethyl ketone peroxide, methyl isobutyl ketone peroxide, acetylacetone peroxide, cyclohexanone peroxide, methylcyclohexanone peroxide and the like; hydroperoxides such as 1,1,3,3-tetramethylbutyl hydroperoxide, cumene hydroperoxide, tert-butyl hydroperoxide and the like; diacyl peroxides such as diisobutyryl peroxide, bis-3,5,5-trimethylhexanol peroxide, lauroyl peroxide, benzoyl peroxide, m-toluylbenzoyl peroxide and the like; dialkyl peroxides such as dicumyl peroxide, 2,5-dimethyl-2,5-di(tert-butylperoxy)hexane, 1,3-bis(tert-butylperoxyisopropyl)hexane, tert-butylcumyl peroxide, di-tert-butyl peroxide, 2,5-dimethyl-2,5-di(tert-butylperoxy)hexene and the like; peroxyketals such as 1,1-di(tert-butylperoxy-3,5,5-trimethyl)cyclohexane, 1,1-di-tert-butylperoxycyclohexane, 2,2-di(tert-butylperoxy)butane and the like; (4-tert-butylcyclohexyl)peroxy dicarbonate and the like. However, the present invention is not limited to these examples alone. These polymerization initiators may each be used alone, or two or more kinds thereof may be used in combination. While the amount of the polymerization initiator is not particularly limited, it is generally preferably about 0.05-20 parts by mass per 100 parts by mass of the polymerizable polymer components.

A chain transfer agent may also be used to adjust the molecular weight when the polymerizable polymer components are polymerized. The chain transfer agent can be generally used by mixing with the polymerizable polymer components. Examples of the chain transfer agent include those similar to the chain transfer agent used for the aforementioned monomer components. While the amount of the chain transfer agent is not particularly limited, it may be generally about 0.01-10 parts by mass per 100 parts by mass of the polymerizable polymer components.

The polymerization reaction temperature and atmosphere when the polymerizable polymer components are polymerized are not particularly limited. Generally, the polymerization reaction temperature is about 50-120° C. The atmosphere at the time of polymerization reaction is preferably inert gas atmosphere such as nitrogen gas and the like. While the polymerization reaction time of the polymerizable polymer components cannot be decided unconditionally since it varies depending on the temperature of polymerization reaction and the like, it is generally about 3-20 hr.

A reaction solution containing a crosslinked polymer can be obtained by polymerizing polymerizable polymer components. The obtained crosslinked polymer has a crosslinked structure, due to which measurement of the molecular weight thereof becomes difficult.

An average particle size of the crosslinked polymer is preferably 0.1 nm-100 µm, more preferably 0.5 nm-1 µm, further preferably 1 nm-500 nm. The average particle size is a value measured by a laser diffraction particle size distribution measuring apparatus [manufactured by SHIMADZU CORPORATION, product number: SALD7000] and means a volume average diameter.

The protein aggregation inhibitor of the present invention contains the aforementioned crosslinked polymer. In the protein aggregation inhibitor of the present invention, for example, the aforementioned crosslinked polymer and an aqueous solvent may be mixed such that the crosslinked polymer is contained at a desired content, and the aqueous solvent contained in the reaction solution containing the crosslinked polymer may be evaporated.

While the content of the crosslinked polymer (solid content) in the protein aggregation inhibitor of the present invention varies depending on the use of the protein aggregation inhibitor and the like, and cannot be decided unconditionally, it is generally about 3-80 mass %. The content of the crosslinked polymer (solid content) in the protein aggregation inhibitor of the present invention can be easily adjusted by adding a solvent to the protein aggregation inhibitor or evaporating the solvent contained in the protein aggregation inhibitor.

In addition, the protein aggregation inhibitor of the present invention may contain an additive and the like according to the use object of the protein aggregation inhibitor of the present invention, as long as the object of the present invention is not inhibited.

As explained above, since the protein aggregation inhibitor of the present invention can inhibit aggregation of protein, it is expected to be used for various applications where inhibition of protein aggregation is desired such as preservative for enzyme, antibody drug, in vivo amyloid aggregation inhibitor and the like.

The present invention provides a method for preventing protein aggregation, including mixing a protein, a solvent or dispersion medium, and the aforementioned protein aggregation inhibitor. In this method, the amount of the crosslinked polymer contained in the protein aggregation inhibitor is preferably 10-200 parts by mass, more preferably 50-100 parts by mass, per 1 part by mass of the protein.

Examples of the solvent or dispersion medium include phosphate buffered saline (PBS), water, tris buffer and the like.

Examples of the protein include lysozyme, albumin, globulin, prolamin, glutelin, cytokine, insulin, antibody, membrane protein, glycoprotein and the like.

The content of a protein in a mixture containing the protein, a solvent or dispersion medium, and the aforementioned protein aggregation inhibitor is preferably 0.001-20 mass %, more preferably 0.01-10 mass %.

EXAMPLES

The present invention is explained in more detail in the following by referring to Examples. However, the present invention is not limited to the Examples alone.

Preparation Example 1

In a 1 L flask provided with a stirring rod, a dimroth, a thermometer and a nitrogen gas introducing tube, 3-[(3-acrylamidopropyl)dimethylammonio]propane-1-sulfonate (12 mmol), 2-(dodecylthiocarbonothioylthio)-2-methylpropionic acid (0.6 mmol) and azobisisobutyronitrile (0.12 mmol) as a polymerization initiator were dissolved in a mixed solvent (60 mL) of methanol (45 mL) and water (15 mL) to give a solution. The obtained solution was placed in a flask, the contents of the flask were heated to 70° C. while introducing a nitrogen gas into the flask, and the mixture was stirred for 1 hr. Thereafter, the monomer components in the flask were polymerized for 6 hr to give a reaction mixture. The obtained reaction mixture was collected by filtration, washed with methanol and water and dried to give a sulfobetaine polymer.

Then, the number average molecular weight of the obtained sulfobetaine polymer was examined by gel permeation chromatography (hereinafter to be referred to as GPC) analysis apparatus [manufactured by Phenomenex, Ink., trade name: BioSeps2000] and high performance liquid chromatography data system [manufactured by SHIMADZU CORPORATION, differential refractometer detector]. As a result, the number average molecular weight of the sulfobetaine polymer was 5,500.

When the number average molecular weight of the sulfobetaine polymer obtained above was examined by GPC, 0.1 M aqueous sodium bromide solution (pH: 7.4) was used as a developing solution. In addition, pullulan manufactured by Showa Denko K.K. was used as the standard solution.

Preparation Example 2

In a 1 L flask provided with a stirring rod, a dimroth, a thermometer and a nitrogen gas introducing tube, 3-[(3-acrylamidopropyl)dimethylammonio]propane-1-sulfonate (120 mmol), 2-(dodecylthiocarbonothioylthio)-2-methylpropionic acid (0.6 mmol) and azobisisobutyronitrile (0.12 mmol) as a polymerization initiator were dissolved in a mixed solvent (60 mL) of methanol (45 mL) and water (15 mL) to give a solution. The obtained solution was placed in a flask, the contents of the flask were heated to 70° C. while introducing a nitrogen gas into the flask, and the mixture was stirred for 1 hr. Thereafter, the monomer components in the flask were polymerized for 6 hr to give a reaction mixture. The obtained reaction mixture was collected by filtration, washed with methanol and water and dried to give a sulfobetaine polymer.

The number average molecular weight of the obtained sulfobetaine polymer was examined in the same manner as in Preparation Example 1. As a result, the number average molecular weight of the sulfobetaine polymer was 36,200.

Example 1

The sulfobetaine polymer (0.2 g) obtained in Preparation Example 1, 3-[(3-acrylamidopropyl)dimethylammonio]propane-1-sulfonate (1.477 g), ethylene glycol dimethacrylate (22 mg, 21 µL) and 4,4'-azobis-(4-cyanovaleric acid) (4 mg) as a polymerization initiator were dissolved in pure water (50 mL) to give a solution. The obtained solution was placed in a flask, the contents of the flask were heated to 70° C. while introducing a nitrogen gas into the flask for 1 hr, and the mixture was stirred. Thereafter, the monomer components in the flask were polymerized for 24 hr to give a reaction mixture. The obtained reaction mixture was collected by filtration, washed with methanol and water and dried to give a crosslinked polymer.

The crosslinked polymer obtained above was dissolved in water to prepare a 10 mass % aqueous crosslinked polymer solution. The crosslinked polymer was dissolved in water to become a nanogel form, and apparently, a uniform solution was obtained. The aforementioned solution was used as a protein aggregation inhibitor. A lysozyme-containing phosphate buffered saline (PBS) was added to the obtained protein aggregation inhibitor, and they were mixed to give a solution (amount of crosslinked polymer per 1 part by mass of protein (lysozyme): 100 parts by mass, content of protein (lysozyme) in the solution: 0.05 mass %). The obtained solution was visually observed to find no aggregation of lysozyme.

The solution (100 µL) obtained above and a 0.25 mg/mL phosphate buffered saline (2 mL) of a bacterium (*Micrococcus lysodeikticus*) susceptible to bacteriolysis by lysozyme were placed in a cuvette and they were sufficiently mixed. The absorbance of the obtained mixture was measured by a spectrophotometer [SHIMADZU CORPORATION, product number: UV-1600PC] at a wavelength of 600 nm at room temperature for the absorbance before stirring and the absorbance after stirring for 6 min, and a decrease in the absorbance before heating (=absorbance before stirring−absorbance after stirring for 6 min) was determined.

Then, the mixture obtained above was heated at 90° C. for 30 min, cooled to room temperature and a decrease in the absorbance after heating (=absorbance before stirring−absorbance after stirring for 6 min) was determined in the same manner as above.

From the decreases in the absorbance before and after heating determined above, the remaining lysozyme activity (%) was determined based on the formula.

$$[\text{remaining lysozyme activity (\%)}] = ([\text{decrease in absorbance after heating}] \div [\text{decrease in absorbance before heating}]) \times 100$$

As a result, the remaining lysozyme activity was 25%.

Example 2

The sulfobetaine polymer (0.2 g) obtained in Preparation Example 1, 3-[(3-acrylamidopropyl)dimethylammonio]propane-1-sulfonate (1.477 g), butyl methacrylate (39.7 mg, 44.4 µL), ethylene glycol dimethacrylate (22 mg, 21 µL) and 4,4'-azobis-(4-cyanovaleric acid) (4 mg) as a polymerization initiator were dissolved in a mixed solvent (60 mL) of water (50 mL) and methanol (10 mL) to give a solution. The obtained solution was placed in a flask, the contents of the flask were heated to 70° C. while introducing a nitrogen gas into the flask for 1 hr, and the mixture was stirred. Thereafter, the monomer components in the flask were polymerized for 24 hr to give a reaction mixture. The obtained reaction mixture was collected by filtration, washed with water and dried to give a crosslinked polymer.

The crosslinked polymer obtained above was dissolved in water to prepare a 10 mass % aqueous crosslinked polymer solution. The crosslinked polymer was dissolved in water to become a nanogel form, and apparently, a uniform solution was obtained. The aforementioned solution was used as a protein aggregation inhibitor. A lysozyme-containing phosphate buffered saline (PBS) was added to the obtained protein aggregation inhibitor, and they were mixed to give a solution (amount of crosslinked polymer per 1 part by mass of protein (lysozyme): 100 parts by mass, content of protein (lysozyme) in the solution: 0.05 mass %). The obtained solution was visually observed to find no aggregation of lysozyme.

Then, a protein aggregation inhibitory effect of the aforementioned protein aggregation inhibitor was examined in the same manner as in Example 1. As a result, the remaining lysozyme activity was 31%.

Example 3

The sulfobetaine polymer (0.2 g) obtained in Preparation Example 1, 3-[(3-acrylamidopropyl)dimethylammonio]propane-1-sulfonate (1.477 g), butyl methacrylate (79.5 mg, 88.8 µL), ethylene glycol dimethacrylate (22 mg, 21 µL) and 4,4'-azobis-(4-cyanovaleric acid) (4 mg) as a polymerization initiator were dissolved in a mixed solvent (60 mL) of water (50 mL) and methanol (10 mL) to give a solution. The obtained solution was placed in a flask, the contents of the flask were heated to 70° C. while introducing a nitrogen gas into the flask for 1 hr, and the mixture was stirred. Thereafter, the monomer components in the flask were polymerized for 24 hr to give a reaction mixture. The obtained reaction mixture was collected by filtration, washed with water and dried to give a crosslinked polymer.

Using the crosslinked polymer obtained above as a protein aggregation inhibitor, a protein aggregation inhibitory effect of the protein aggregation inhibitor was examined in the same manner as in Example 1. As a result, the remaining lysozyme activity was 40%.

The crosslinked polymer obtained above was dissolved in water to prepare a 10 mass % aqueous crosslinked polymer solution. The crosslinked polymer was dissolved in water to become a nanogel form, and apparently, a uniform solution was obtained. The aforementioned solution was used as a protein aggregation inhibitor. A lysozyme-containing phosphate buffered saline (PBS) was added to the obtained protein aggregation inhibitor, and they were mixed to give a solution (amount of crosslinked polymer per 1 part by mass of protein (lysozyme): 100 parts by mass, content of protein (lysozyme) in the solution: 0.05 mass %). The obtained solution was visually observed to find no aggregation of lysozyme.

Example 4

The sulfobetaine polymer (0.2 g) obtained in Preparation Example 2, 3-[(3-acrylamidopropyl)dimethylammonio]propane-1-sulfonate (1.477 g), ethylene glycol dimethacrylate (22 mg, 21 µL) and 4,4'-azobis-(4-cyanovaleric acid) (4 mg) as a polymerization initiator were dissolved in pure water (50 mL) to give a solution. The obtained solution was placed in a flask, the contents of the flask were heated to 70° C. while introducing a nitrogen gas into the flask for 1 hr, and the mixture was stirred. Thereafter, the monomer components in the flask were polymerized for 24 hr to give a reaction mixture. The obtained reaction mixture was collected by filtration, washed with methanol and water and dried to give a crosslinked polymer.

The crosslinked polymer obtained above was dissolved in water to prepare a 10 mass % aqueous crosslinked polymer solution. The crosslinked polymer was dissolved in water to become a nanogel form, and apparently, a uniform solution was obtained. The aforementioned solution was used as a protein aggregation inhibitor. A lysozyme-containing phosphate buffered saline (PBS) was added to the obtained protein aggregation inhibitor, and they were mixed to give a solution (amount of crosslinked polymer per 1 part by mass of protein (lysozyme): 100 parts by mass, content of protein (lysozyme) in the solution: 0.05 mass %). The obtained solution was visually observed to find no aggregation of lysozyme.

Then, a protein aggregation inhibitory effect of the aforementioned protein aggregation inhibitor was examined in the same manner as in Example 1. As a result, the remaining lysozyme activity was 37%.

Example 5

The sulfobetaine polymer (0.2 g) obtained in Preparation Example 2, 3-[(3-acrylamidopropyl)dimethylammonio]propane-1-sulfonate (1.477 g), butyl methacrylate (39.7 mg, 44.4 µL), ethylene glycol dimethacrylate (22 mg, 21 µL) and 4,4'-azobis-(4-cyanovaleric acid) (4 mg) as a polymerization initiator were dissolved in a mixed solvent (60 mL) of water (50 mL) and methanol (10 mL) to give a solution. The obtained solution was placed in a flask, the contents of the flask were heated to 70° C. while introducing a nitrogen gas into the flask for 1 hr, and the mixture was stirred. Thereafter, the monomer components in the flask were polymerized for 24 hr to give a reaction mixture. The obtained reaction mixture was collected by filtration, washed with water and dried to give a crosslinked polymer.

The crosslinked polymer obtained above was dissolved in water to prepare a 10 mass % aqueous crosslinked polymer solution. The crosslinked polymer was dissolved in water to become a nanogel form, and apparently, a uniform solution was obtained. The aforementioned solution was used as a protein aggregation inhibitor. A lysozyme-containing phosphate buffered saline (PBS) was added to the obtained protein aggregation inhibitor, and they were mixed to give a solution (amount of crosslinked polymer per 1 part by mass of protein (lysozyme): 100 parts by mass, content of protein (lysozyme) in the solution: 0.05 mass %). The obtained solution was visually observed to find no aggregation of lysozyme.

Then, a protein aggregation inhibitory effect of the aforementioned protein aggregation inhibitor was examined in the same manner as in Example 1. As a result, the remaining lysozyme activity was 52%.

Example 6

The sulfobetaine polymer (0.2 g) obtained in Preparation Example 2, 3-[(3-acrylamidopropyl)dimethylammonio]propane-1-sulfonate (1.477 g), butyl methacrylate (79.5 mg, 88.8 µL), ethylene glycol dimethacrylate (22 mg, 21 µL) and 4,4'-azobis-(4-cyanovaleric acid) (4 mg) as a polymerization initiator were dissolved in a mixed solvent (60 mL) of water (50 mL) and methanol (10 mL) to give a solution. The obtained solution was placed in a flask, the contents of the flask were heated to 70° C. while introducing a nitrogen gas into the flask for 1 hr, and the mixture was stirred. Thereafter, the monomer components in the flask were polymerized for 24 hr to give a reaction mixture. The obtained reaction mixture was collected by filtration, washed with water and dried to give a crosslinked polymer.

The crosslinked polymer obtained above was dissolved in water to prepare a 10 mass % aqueous crosslinked polymer solution. The crosslinked polymer was dissolved in water to become a nanogel form, and apparently, a uniform solution was obtained. The aforementioned solution was used as a protein aggregation inhibitor. A lysozyme-containing phosphate buffered saline (PBS) was added to the obtained protein aggregation inhibitor, and they were mixed to give a solution (amount of crosslinked polymer per 1 part by mass of protein (lysozyme): 100 parts by mass, content of protein (lysozyme) in the solution: 0.05 mass %). The obtained solution was visually observed to find no aggregation of lysozyme.

Then, a protein aggregation inhibitory effect of the aforementioned protein aggregation inhibitor was examined in the same manner as in Example 1. As a result, the remaining lysozyme activity was 66%.

Comparative Example 1

The sulfobetaine polymer obtained in Preparation Example 1 was dissolved in water to prepare a 10 mass % aqueous crosslinked polymer solution. The obtained solution was used as a protein aggregation inhibitor. A lysozyme-containing phosphate buffered saline (PBS) was added to the obtained protein aggregation inhibitor, and they were mixed to give a solution (amount of sulfobetaine polymer per 1 part by mass of protein (lysozyme): 100 parts by mass, content of protein (lysozyme) in the solution: 0.05 mass %).

A protein aggregation inhibitory effect of the aforementioned protein aggregation inhibitor was examined in the same manner as in Example 1. As a result, the remaining lysozyme activity was 2%.

From the above results, it is clear that the protein aggregation inhibitor obtained in each Example can maintain lysozyme activity and effectively inhibit protein aggregation.

INDUSTRIAL APPLICABILITY

The protein aggregation inhibitor of the present invention can maintain lysozyme activity and effectively inhibit protein aggregation. Therefore, it is expected to be used for various applications where inhibition of protein aggregation is desired such as preservative for enzyme, antibody drug, in vivo amyloid aggregation inhibitor and the like.

Therefore, the protein aggregation inhibitor of the present invention is expected to be used in various fields such as food processing field, antibody drug field, transplantation therapy field, enzyme production field, pharmaceutical-related field and the like.

This application is based on a patent application No. 2016-108846 filed in Japan, the contents of which are incorporated in full herein.

The invention claimed is:

1. A protein aggregation inhibitor for use in preventing aggregation of a protein, the inhibitor comprising a crosslinked polymer obtained by polymerizing polymerizable polymer components comprising
    a sulfobetaine polymer obtained by polymerizing monomer components comprising a sulfobetaine monomer, the sulfobetaine monomer, and
    a crosslinkable monomer,
    wherein the sulfobetaine monomer is represented by the formula (I):

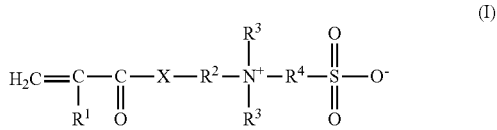

wherein $R^1$ is a hydrogen atom or a methyl group, $R^2$ is an alkylene group having 1-4 carbon atoms, $R^3$ is an alkyl group having 1-4 carbon atoms, $R^4$ is an alkylene group having 1-4 carbon atoms, and X is an —NH— group or an —O— group.

2. The protein aggregation inhibitor according to claim 1, wherein the monomer components further comprise a thiocarbonylthio group-containing compound having at least one carboxyl group.

3. The protein aggregation inhibitor according to claim 1, wherein the polymerizable polymer components further comprise a hydrophobic monomer.

4. A method of producing a protein aggregation inhibitor for use in preventing aggregation of a protein and comprising a crosslinked polymer, the method comprising
    polymerizing monomer components comprising a sulfobetaine monomer, and
    polymerizing polymerizable polymer components comprising the resulting sulfobetaine polymer, the sulfobetaine monomer, and a crosslinkable monomer,
    wherein the sulfobetaine monomer is represented by the formula (I):

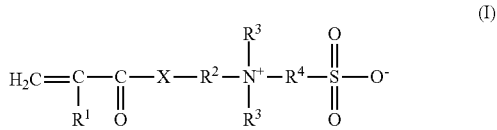

wherein $R^1$ is a hydrogen atom or a methyl group, $R^2$ is an alkylene group having 1-4 carbon atoms, $R^3$ is an alkyl group having 1-4 carbon atoms, $R^4$ is an alkylene group having 1-4 carbon atoms, and X is an —NH— group or an —O— group.

5. The method according to claim 4, wherein the monomer components are polymerized in the presence of a thiocarbonylthio group-containing compound having at least one carboxyl group.

6. The method according to claim 4, wherein the polymerizable polymer components further comprise a hydrophobic monomer.

* * * * *